US00PP32002P2

(12) United States Plant Patent
LaBonte

(10) Patent No.: US PP32,002 P2
(45) Date of Patent: Jul. 21, 2020

(54) SWEETPOTATO PLANT NAMED 'LA15-527'

(50) Latin Name: ***Ipomoea batatas* (L.) Lam.**
Varietal Denomination: LA15-527

(71) Applicant: The Board of Supervisors of Louisiana State University and Agricultural and Mechanical College, Baton Rouge, LA (US)

(72) Inventor: Don R. LaBonte, Baton Rouge, LA (US)

(73) Assignee: THE BOARD OF SUPERVISORS OF LOUISIANA STATE UNIVERSITY AND AGRICULTURAL AND MECHANICAL COLLEGE, Baton Rouge, LA (US)

( * ) Notice: Subject to any disclaimer, the term of this patent is extended or adjusted under 35 U.S.C. 154(b) by 0 days.

(21) Appl. No.: 16/350,985

(22) Filed: Feb. 8, 2019

(51) Int. Cl.
*A01H 5/06* (2018.01)
*A01H 6/00* (2018.01)

(52) U.S. Cl.
USPC ..... Plt./258

(58) Field of Classification Search
USPC ..... Plt./258, 226, 263.1, 256
CPC ... A01H 5/06; A01H 5/02; A01H 5/12; A01H 5/00; A01H 5/04; A01H 6/00
See application file for complete search history.

*Primary Examiner* — June Hwu
(74) *Attorney, Agent, or Firm* — Baker Donelson

(57) ABSTRACT

A new variety of sweetpotato, identified as 'LA15-527', is disclosed having attractive chartreuse leaves and storage root formation.

3 Drawing Sheets

Genus and species name: *Ipomoea batatas* (L.) Lam.
Variety denomination: 'LA15-527'.

BACKGROUND OF THE INVENTION

Sweetpotatoes, unlike Irish potatoes (*Solanum tuberosum*), are not tuber propagated plants. A "tuber" is a short, thickened portion of an underground branch. Along a tuber "eyes" are found, each of which comprises a ridge bearing a scale-like leaf (analogous to a branch leaf) having minute meristematic buds in the axial of the leaf. By contrast, sweetpotato roots are developmentally and anatomically true roots, lacking meristematic buds, and are not derived from an underground branch. Sweetpotatoes do not form tubers.

SUMMARY OF THE INVENTION

This invention pertains to a new and distinct variety of sweetpotato. This new and distinct sweetpotato variety demonstrates no resistance to Fusarium wilt and southern root-knot nematode, and has ornamental foliage characteristics. It also demonstrates a white-yellow flesh with sometimes purple mottling in the storage root. Leaves are chartreuse and similar to the mostly non-storage root forming 'Marguerite' ornamental variety.

This new and distinct sweetpotato variety is identified as 'LA15-527', and is characterized by ornamental chartreuse foliage, and storage roots with white-yellow flesh and sometimes purple mottling, oblong shape, and light tan skin.

DETAILED BOTANICAL DESCRIPTION

This new variety of sweetpotato, named 'LA15-527', resulted from a cross performed in 2014 between a progeny of 'Marguerite' x LA2001.6 (not patented) and the male parent LA 08-36 (not patented). The female parent ('Marguerite' x 'LA2001.6') has green, deep lobed leaves and is profusely flowering. The male parent ('LA 08-36') has chartreuse, spade shaped leaves. 'LA15-527' was developed to provide a variety with ornamental foliage characteristics similar to 'Marguerite', but with storage root formation. 'Marguerite' infrequently produces a fleshy storage root.

Figure 3:
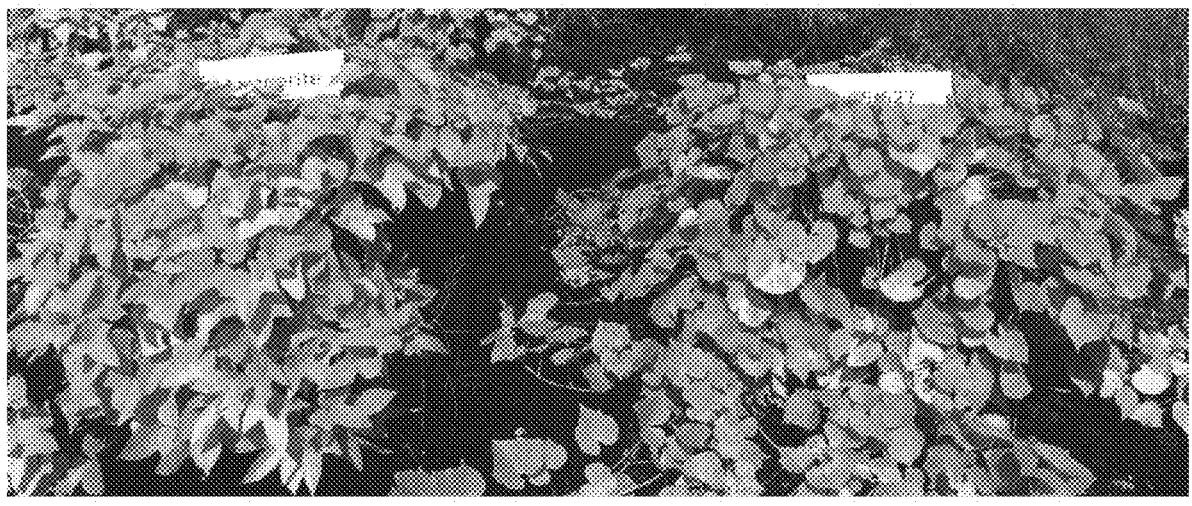
FIG. 3 is a color photograph of the canopy biomass of the novel variety of sweetpotato identified as 'LA15-527' (right) and 'Marguerite' (left).

Plants of 'LA15-527' and variety 'Marguerite' can be differentiated. Leaves of 'LA15-527' are chartreuse [10 Y (yellow) (6/10)] and 'Marguerite' in comparison is more yellow [10 Y (yellow) (6/8)] as depicted in FIG. 3. Both have entire leaves. 'LA15-527' has a cordate base to the leaf and 'Marguerite' is slightly hastate. 'LA15-527' forms fleshy storage roots while 'Marguerite' infrequently produces storage roots. Color terminology used herein is in accordance with the MUNSELL® Book of Color (2003 Edition, Munsell Color, GretagMacbeth LLC, 617 Little Britain Road, New Windsor, N.Y. 12553-6148). The color descriptions and color illustrations are as nearly true as is reasonably possible. However, it is understood that both color and other phenotypic expressions described herein may vary from plant to plant with differences in growth, environment and cultural conditions, without any change in the genotype of the variety 'LA15-527'.

'LA15-527' roots were stored during the winter in Baton Rouge, La. 'LA15-527' was planted the following spring, resulting in approximately 8-10 sprouts per root. Cuttings from the sprouts were transplanted successfully for asexual reproduction in Baton Rouge, La. Asexual propagation of the new cultivar by cuttings has shown that the unique features of this new sweetpotato were stable and that the plant reproduced true to type in successive generations of asexual propagation. Plants described herein were 90 days in age from planting in full sun field plantings.

Figure 1:
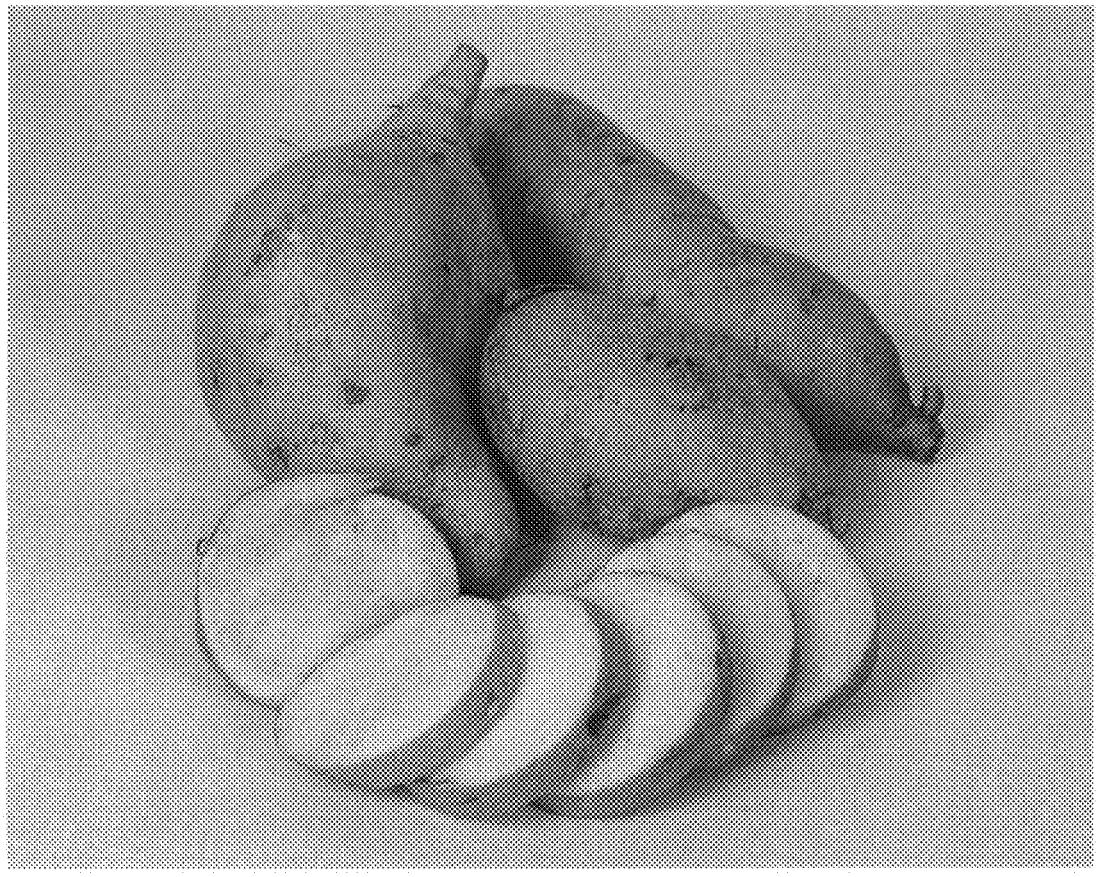
FIG. 1 is a color photograph of the fleshy root form of the novel variety of sweetpotato identified as 'LA15-527'.
Figure 2:
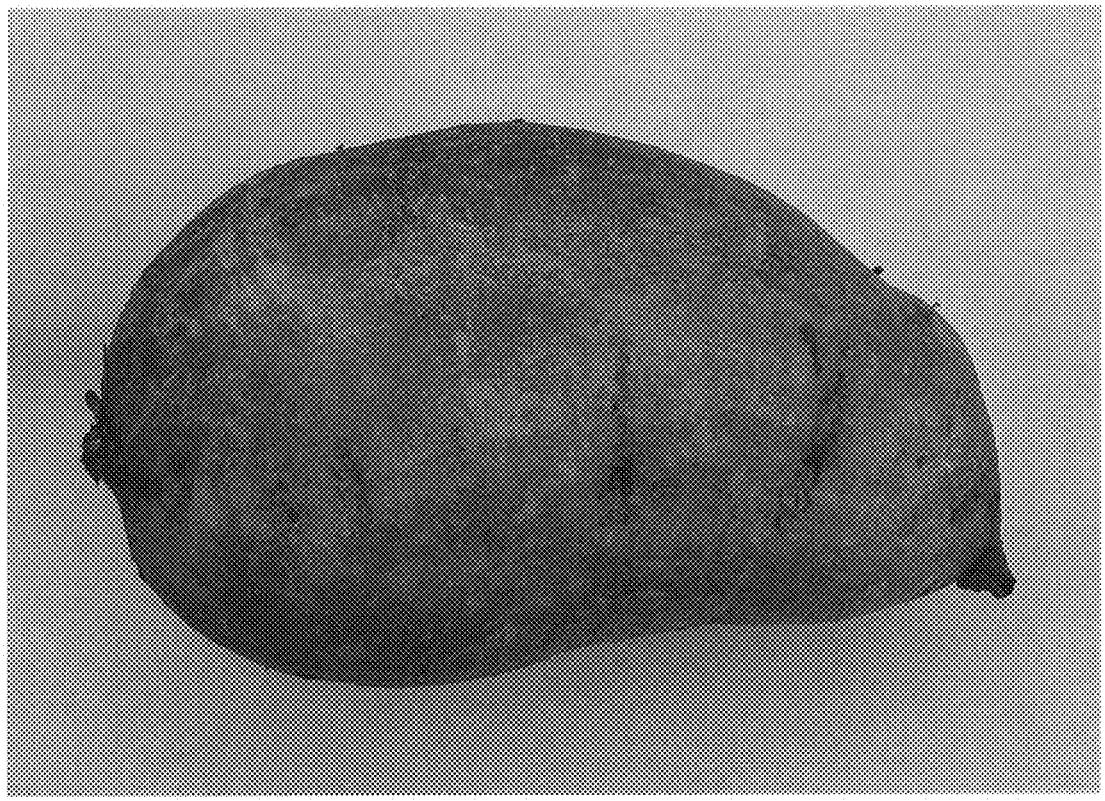
FIG. 2 is a color photograph of the fleshy root form of the 'Marguerite' variety of sweetpotato.

FIG. 1 depicts the fleshy root form of the 'LA15-527' sweetpotato. The skin is light tan at harvest and after several months of storage as shown in Table 1. MUNSELL® Book of Color values for skin and flesh for 'LA15-527' and 'Marguerite' are shown in Table 1. No eyes or longitudinal grooving is present. The 'Marguerite' sweetpotato is depicted in FIG. 2. The skin for 'LA15-527' and 'Marguerite' was smooth. The 'LA15-527' cortex was 4.1 mm in depth and the color similar throughout for the white-yellow flesh; some fleshy roots have purple mottling. The skin of 'Marguerite' is red-purple and flesh similar to 'LA15-527' without purple mottling.

TABLE 1

| Variable | Variety | Color |
|---|---|---|
| Skin | 'LA15-527' | 5 Y (yellow) R (red) 8/4 |
| | 'Marguerite' | 2.5 R (red) P (purple) 6/6 |
| Flesh | 'LA15-527' | 5 Y (yellow) 9/2 |
| | 'LA15-527' (purple mottle) | 2.5 R (red) P (purple) 7/4 |
| | 'Marguerite' | 7.5 Y (yellow) 9/2 |

FIG. 3 depicts the canopy biomass of 'LA15-527' and 'Marguerite' sweetpotato. 'LA15-527' has round, green-stemmed vines which change little [2.5 G (green) Y (yellow) (6/10)] from the apex and extends to the crown of the roots. Stems exposed to bright sun take on a reddish hue [5 R (red) (4/4)]. The first 4 cm from the apex is slightly pubescent before becoming glabrous. The 'LA15-527' canopy biomass appears less than 'Marguerite'. The 'LA15-527' canopy architecture was semi-upright and average (23 cm) in height from the soil surface and less than 'Marguerite'. For 'LA15-527', three main vines arose from the main stem near the soil surface. The stem giving rise to these vines was 1.3 cm in diameter; the 3 lateral vines were 121 cm in length with diameters of about 0.4 cm at 65 cm from the base and diameters of about 0.25 cm at the first internode of the first fully developed leaf from the apex. The spread is less than 'Marguerite' but average compared to other sweetpotato varieties. Six lateral branches arose from each of the main vines. At the first internode from the apex, the internode length was about 1.3 cm between the first and second fully developed leaves. Internode lengths for other sections of the vine averaged about 3.1 cm. Unfolded immature leaves were light green [2.5 G (green) Y (yellow) (6/8)] for the adaxial and a more yellow [10 Y (yellow) 6/10)] abaxial surface, which change little over 7 nodes from the apex. The abaxial leaves differ slightly [2.5 G (green) Y (yellow) (6/4)]. Anthocyanin pigmentation and pubescence were absent from the stem tips and unfolded immature leaves. Mature leaves five nodes from the apex had an acute apex and mostly a cordate base. Leaf margins are smooth. Mature leaves were about 7.4 cm long and 7.7 cm wide with margins having 5 very shallow leaf lobes and round in appearance. Leaves were glabrous for abaxial and adaxial sides, without undulations, and pliable. Mature adaxial and abaxial veins were in a pinnate venation pattern and weak purple [7.5 R (red) P (purple) (4/6)] and fades as it reaches the apex of the leaf. This differs from immature leaves with no purple hue to veins. The petiole was green [2.5 G (green) Y (yellow) (6/10)]. A weak purple [7.5 R (red) P (purple) (4/6)] marking was at the base of the entire leaf junction with the petiole and extends 0.5 cm on the petiole. The round glabrous petiole was 3.0 cm long at five nodes from the apex, and 2 mm in diameter at 5 cm from the leaf junction. The dormant nodal meristem was green [2.5 G (green) Y (yellow) (6/10)].

Flowers are uncommon in 'LA15-527'. A typical inflorescence of 'LA15-527' displayed two flowers per peduncle. Peduncles were green [10 Y (yellow) (6/8)], about 4.2 cm long, and about 3 mm in diameter. Individual flowers were about 3.5 cm long from the base of the calyx, and the corolla was 2.5 cm wide at the opening. The fused flower petals formed a pentagonal pattern with smooth edges. The inner throat of the corolla was purple [7.5 P (purple) (3/8)]. The inner and outer limbs of the corolla (corollas outermost area, distal from the calyx) were light purple [7.5 P (purple) (7/4)]. The five sepals comprising the calyx were elliptic with a cordate apex and green [2.5 G (green) Y (yellow) (6/6)]; three of these sepals were about 10 mm long and 4 mm wide. Two other sepals (interspersed) were about 6 mm long and 2.7 mm wide. Sepal margins were entire. Stigmata were about 1.4 cm long and light purple [7.5 R (red) P (purple) (8/6)] at the base before fading. Five stamens were inferior to the stigmata. A slight fragrance was present. Mature seed capsules are round and 6-6.3 mm in length and width, and seeds are 3.5 mm round. One black [neutral 1.75] seed is produced on average per capsule.

EXAMPLE 1

Tests Conducted

To confirm that 'LA15-527' was a new ornamental variety with storage roots, controlled tests (e.g., pathogen responses and yield) were conducted in Baton Rouge, La. Diseases that commonly affect the growth of sweetpotatoes were selected to test for pathogen responses in both varieties. 'LA15-527' was very susceptible to Fusarium wilt or stem rot caused by *Fusarium oxysporum* Schlect. f sp. *batatas* (Wollenw.) Snyd. & Hans.

'LA15-527' has not been tested for novel insect resistance.

Nematode reproduction was measured in greenhouse tests. 'LA15-527' was susceptible to race 3 of the southern root-knot nematode, *Meloidogyne incognita* (Kofoid & White 1919) Chitwood 1949. Resistance reactions for 'Marguerite' are unknown.

'LA15-527' is drought and heat tolerant like 'Marguerite' and succumbs to death at freezing like 'Marguerite'.

To determine yield production, three sweetpotato plants of 'LA15-527' were transplanted to 2.65 L pots in 2018 in Baton Rouge, La. containing commercial potting soil. Pots were watered daily to field capacity. Storage roots are mostly oblong and thus do not fit U.S grades of sweetpotato. The average yield was 0.5 kg per pot. Most roots measure 90-135 mm long and 27-44 mm in diameter. Roots tend to be in two weight classes (50-80 g and 120-150 g) and small. 'LA15-

527' is not intended for commercial storage root production, but intended as an ornamental with edible storage roots.

'LA15-527' should be a valuable commercial ornamental sweetpotato variety. 'LA15-527' represents a unique canopy type which produces edible storage roots.

We claim:

1. A new and distinct variety of *Ipomoea batatas* plant named 'LA15-527' as described and illustrated in the specification herein.

* * * * *